United States Patent [19]
Salter

[11] Patent Number: 5,487,982
[45] Date of Patent: Jan. 30, 1996

[54] METHOD OF OBTAINING IMMUNOGENIC PEPTIDES FROM CELLS EXPRESSING TEMPERATURE-SENSITIVE MUTANTS OF MAJOR HISTOCOMPATIBILITY COMPLEX MOLECULES

[75] Inventor: Russell D. Salter, Pittsburgh, Pa.

[73] Assignee: University of Pittsburgh, Pittsburgh, Pa.

[21] Appl. No.: 65,612

[22] Filed: May 21, 1993

[51] Int. Cl.$^6$ .............................. C07K 1/00; C07K 2/00; C12P 21/00

[52] U.S. Cl. ...................... 435/69.1; 435/70.3; 435/70.4; 530/300; 530/333

[58] Field of Search .................................. 435/70.3, 70.4, 435/69.1

[56] References Cited

PUBLICATIONS

Rock et al., J. Immunol. 150:1244–1252 (1993).
Salter, J. Cell Biochem., Suppl. 16 Part D, p. 22 (1992).
Pamer, et al., Nature 353:852–854 (1991).

*Primary Examiner*—Robert A. Wax
*Assistant Examiner*—Eric Grimes
*Attorney, Agent, or Firm*—Reed Smith Shaw & McClay

[57] ABSTRACT

Genetically engineered temperature-sensitive class I HLA mutants are provided which can be used in a method to obtain peptides which are bound to MHC class I molecules on the surfaces of cells that are transfected with the mutant genes.

6 Claims, 5 Drawing Sheets

PEPTIDE RELEASE FROM A2M242

METHOD OF OBTAINING IMMUNOGENIC PEPTIDES FROM CELLS EXPRESSING TEMPERATURE-SENSITIVE MUTANTS OF MAJOR HISTOCOMPATIBILITY COMPLEX MOLECULES

FIELD OF THE INVENTION

The present invention relates generally to the biosynthesis of temperature-sensitive major histocompatibility complex ("MHC") molecules, and more particularly relates to temperature-sensitive mutants of heavy chains of MHC class I molecules. According to the invention certain, preferably, immunogenic peptides that are expressed at the cell surface of viable cells that harbor genes for the temperature-sensitive mutants may be released under certain conditions. Peptides so obtained may find use in the development of viral or tumor vaccines, or alternatively as a means to treat autoimmune diseases.

BACKGROUND OF THE INVENTION

Major histocompatibility complex ("MHC") molecules a central role in T cell mediated immune play responses. T lymphocyte ("T cell") antigen receptors ("TCR") recognize endogenously processed fragments of antigens that are presented to T cells in association with major histocompatibility complex ("MHC") class I or class II molecules.

An individual's T cells recognize and are activated by protein antigens only if a fragment of the antigen is properly presented on the surface of a target cell. The antigen presentation process that allows an antigen to be recognized by a T cell requires that the antigen be associated with either (MHC) class I histocompatibility molecules for presentation to cytotoxic T lymphocytes ("CTLs") or class II histocompatibility molecules for presentation to helper T cells. Other T cell subsets such as γ/δ (gamma-delta) T cells (CD4−, CD8−) may recognize alternate "peptide presenting" molecules not encoded in the MHC, such as CDl, etc.

The subset of T cells denoted CD8+ recognize antigenic determinants/epitopes that are associated with class I histocompatibility molecules. The other subset of T cells, CD4+ cells, recognize antigenic determinants/epitopes that are associated with class II histocompatibility molecules. The antigenic determinants/ epitopes that are presented on the surface of cells in association with MHC molecules are also known as T cell epitopes.

The study of CD8+T cell recognition of target cells has been extensive since the early 1970's when it was demonstrated that CTL recognition of viral-infected autologous target cells requires the presence of self class I MHC molecules. Thus such recognition of target cells by CD8+T cells is referred to as being MHC class I-restricted. Zinkernagel, R. M., et al., *Adv. Immunol.* 27:51 (1979); Doherty, P. C., et al., *Adv. Cancer Res.* 42:1 (1984); and Zinkernagel, R. M., et al., *Nature* 248:701 (1974), the disclosures of which are incorporated herein by reference. It was later shown that virus-specificity of CTL's is directed against vital protein-derived peptide sequences that are presented by infected cell MHC class I molecules to CD8+T cells. See for example, Townsend, A., et al., *Cell* 42:457 (1985) and Townsend, A., et al., *Cell* 44:959 (1986), the disclosures of which are incorporated herein by reference.

Class I molecules (HLA-A, B, C in humans) are composed of two polypeptide chains: a heavy chain which spans the membrane bilayer, and the non-covalently attached light chain, $\beta_2$m microglobin ("$\beta_2$m"). The extracellular portion of the heavy chain is divided into three domains, $\alpha_1$, $\alpha_2$, and $\alpha_3$, each being approximately 90 amino acids. It is not known if free heavy chains inside the cell can bind peptides, or if $\beta_2$m must first bind to the heavy chains.

As noted above, it is not the entire antigen that is presented by target cells and recognized by CD8+ cells, but rather what is presented and recognized are small endogenously processed peptides that are generated from antigens by intracellular degradation pathways in either the cytosol or the endoplasmic reticulum ("ER") of the target cell. Such processed peptides bind to newly synthesized class I heavy chains either before or after binding to $\beta_2$m in the secretory compartment. See, for example, Yewdell, J.W., et al., *Science* 244:1072 (1989); Townsend, A., et al., *Cell* 62:285 (1990); and Nuchtern, J.G., et al., *Nature* 339:223 (1989), the disclosures of which are incorporated herein by reference. The processed peptide is bound to the class I heavy chain-light chain dimer molecule via the class I antigen binding site/peptide cleft. The complex thereby generated is a transport competent trimer as reported by Yewdell, J. W., et al., *Science* 244:1072 (1989); Townsend, A., et al., *Cell* 62:285 (1990); and Nuchtern, J. G., et al., *Nature* 339:223 (1989). This class I histocompatibility molecule-processed peptide complex is then transported through the Golgi apparatus, where glycan modification occurs and is expressed on the surface of the target cell where it may be ultimately recognized by T cell clonotypic receptors on CD8+ cells in conjunction with CD8 accessory molecules. See, Rotzschke, O., et al., *Nature* 348:252 (1990); Van Bleek, G. M., et al., *Nature* 348:213 (1990); Rotzschke, O., et al., *Science* 249:283 (1990); and Falk, K., et al., *Nature* 348:248 (1990), the disclosures of which are incorporated herein by reference.

Mutant cell lines such as RMA-S, .174, and a somatic cell hybrid of .174 called T2 have been reported in which class I molecules are synthesized but are not stably expressed at the plasma membrane. See, for example, Salter, R. D., et al., *Immunogenetics* 2 1:235 (1985); Salter, R. D., et al., *EMBO J.* 5:943 (1986), the disclosures of which are incorporated herein by reference. Treatment of such cells with synthetic peptides was found to increase the levels of serologically detectable class I molecules at the cell surface. See, for example, Townsend, A., et al., *Nature* 240:443 (1989); Cerundolo, V., et al., *Nature* 345:449 (1990), the disclosures of which are incorporated herein by reference. It was recently shown in murine RMA-S cells that "empty" class I molecules, consisting of heavy chains and $\beta_2$m but lacking processed peptide that appeared at the cell surface after growth at 26° C., could bind exogenous peptides more readily than class I molecules on normal RMA-S cells. Ljunggren H. G., et al., *Nature* 346:476 (1990); and Towsend, A., et al., *Cell* 62:285, (1990), the disclosures of which are incorporated herein by reference.

Recently, peptides have been isolated from the antigen binding sites of human and murine class I and class II molecules and directly sequenced. Two principal methods have been used to isolate such peptides. In one of the two methods total cellular extraction of such peptides is carried out in pH 2.0 trifluoroacetic acid ("TFA"). This method results in cell cytolysis and release of total cytosolic peptides, only a fraction of which are actually class I-related. This method also typically employs protease inhibitors since cell cytolysis results in the release of proteolytic enzymes that can alter or destroy peptides of potential interest. See, Rotzschke, O., et al., *Nature* 348:252 (1990), and Falk, K., et al., *Nature* 348:248 (1990), the disclosures of which are incorporated herein by reference. The second isolation method entails acid denaturation of immunoaffinity purified class I-peptide complexes. By contrast with the first method, the second method of peptide isolation is highly class I selective, and even class I allele specific since monoclonal antibodies directed against individual class I allotypes can be used to immunopurify class I complexes. By this latter approach, the majority of known class I-bound peptide sequence data has been acquired. See, for example, Van Bleek, G. M., et al., *Nature* 348:213 (1990); Rotzschke, O., et al., *Science* 249:283 (1990); Madden, D. R., et al., *Nature* 353:326 (1991); Jardetzky, T. S., et al., *Nature* 351:290 (1991); and Nikolic-Zugic, J., et al., *Immunol. Rev.* 10:54 (1991), the disclosures of which are incorporated herein by reference.

The main drawback of these two methods is that since both require cell cytolysis, a large number of starting cells ($10^9$–$10^{11}$) are required from which peptides are extracted after cellular cytolysis in order to obtain sequence grade quantities (approximately 1 pM) of specific peptide. Therefore the application of such techniques are limited to cell types which readily adapt to in vitro cell culture and which proliferate sufficiently well to allow such high cellular yields.

Methods of isolating class I peptide complexes are of additional interest because CD8+ lymphocytes have emerged as being potentially useful in the development of anti-tumor vaccines, which vaccines will ideally provoke anti-tumor immune responses in individuals. To that end, tumor infiltrating lymphocytes (TILs) have been found to be important agents in the generation of cellular immunity through their identification in spontaneously regressing lesions in some patients as reported by Kornstein, M. J., et al. *Cancer Res.* 43:2749 (1983), the disclosure of which is incorporated herein by reference. TILs are also frequently found in non-regressing lesions and when present in high numbers are correlated with a better clinical prognosis. Van Duinen, S. G., et al., *Cancer Res.* 48:1019 (1988), the disclosure of which is incorporated herein by reference. Numerous studies have shown that such TILs display potent anti-melanoma cytolytic activity when they are cultured in vitro with interleukin-2. See, for example, Lotze, M. T., *Pigment Cell* 10:163 (1990), and Rosenberg, S. A., et al., *N. Eng. J. Med.* 319:1676 (1988). Anti-melanoma cytolytic activity is typically associated with CD8+ TIL subpopulations which recognize tumor cells in a class I-restricted manner. The HLA class I antigen, HLA-A2, appears to represent the most common class I restriction element for human melanoma TIL, however, other HLA class I antigens such as HLA-A1, -A10, -A24, -A31, -B44, -B50, and -CW7 have also been identified. The identification of such restriction elements may be important in the development of effective melanoma vaccines.

There remains a need for methods that will efficiently extract class I-associated peptides without affinity purification and acid extraction of class I complexes and which requires fewer cells than the aforedescribed methods.

SUMMARY OF THE INVENTION

Accordingly, it is a primary object of the present invention to provide temperature-sensitive mutants of class I molecules which can be induced or inhibited based on temperature.

It is another object of the invention to provide a method for rapidly obtaining class I-associated peptides from the cell surface of viable class I cells without need for affinity purification or low pH treatment using the aforementioned temperature-sensitive mutants.

Yet another object of the present invention is to provide a method of obtaining T cell epitopes directly from viable cell using 10 fold fewer cells than other methods.

Yet a further object of the present invention is to selectively induce instability of class I molecules via temperature changes.

These and other objects of the present invention are achieved by one or more of the following embodiments.

In one aspect, the invention features a method of obtaining peptides that are bound to class I major histocompatibility complex "MHC" molecules expressed on the cell surfaces of viable cells that have been transfected with a gene for a temperature-sensitive mutant class I molecule, comprising the steps of:

incubating the cells at about 37° C. in culture media;

incubating the cells at about 20°–30° C. to allow expression of MHC-peptide complexes on the surfaces of the cells;

incubating the cells at about 37° C. to cause dissociation of the peptides from the MHC-peptide complexes; and recovering the peptides from the culture media.

In another aspect, the invention features a method of obtaining peptides that are bound to class I MHC molecules expressed on the cell surfaces of viable cells that have at least one MHC-peptide complex presented on the surfaces of the cells, the method comprising:

transfecting cells with mutant genes that code for class I MHC heavy chain molecules such that the expressed class I molecules contain a mutation causing the class I MHC molecules to be unstable at about 37° C. but which are stable at lower temperatures;

inducing the transfected cells to express their class I HLA molecules by shifting the temperature to the range of between about 20°–30° C.;

destabilizing the expressed class I HLA molecules by shifting the temperature to about 37° C.;

and recovering peptide that had been bound to class I molecules.

In preferred embodiments, the gene codes for class I heavy chains that contain a mutation coding for lysine instead of glutamine at position 242 in the $\alpha_3$ domain of the heavy chain.

Other features and advantages of the invention will be apparent from the following description of the preferred embodiment, and from the claims.

DETAILED DESCRIPTION OF THE INVENTION

I. Definitions

Figures 1A, 1B, 1C, 1D, 1E, 1F:
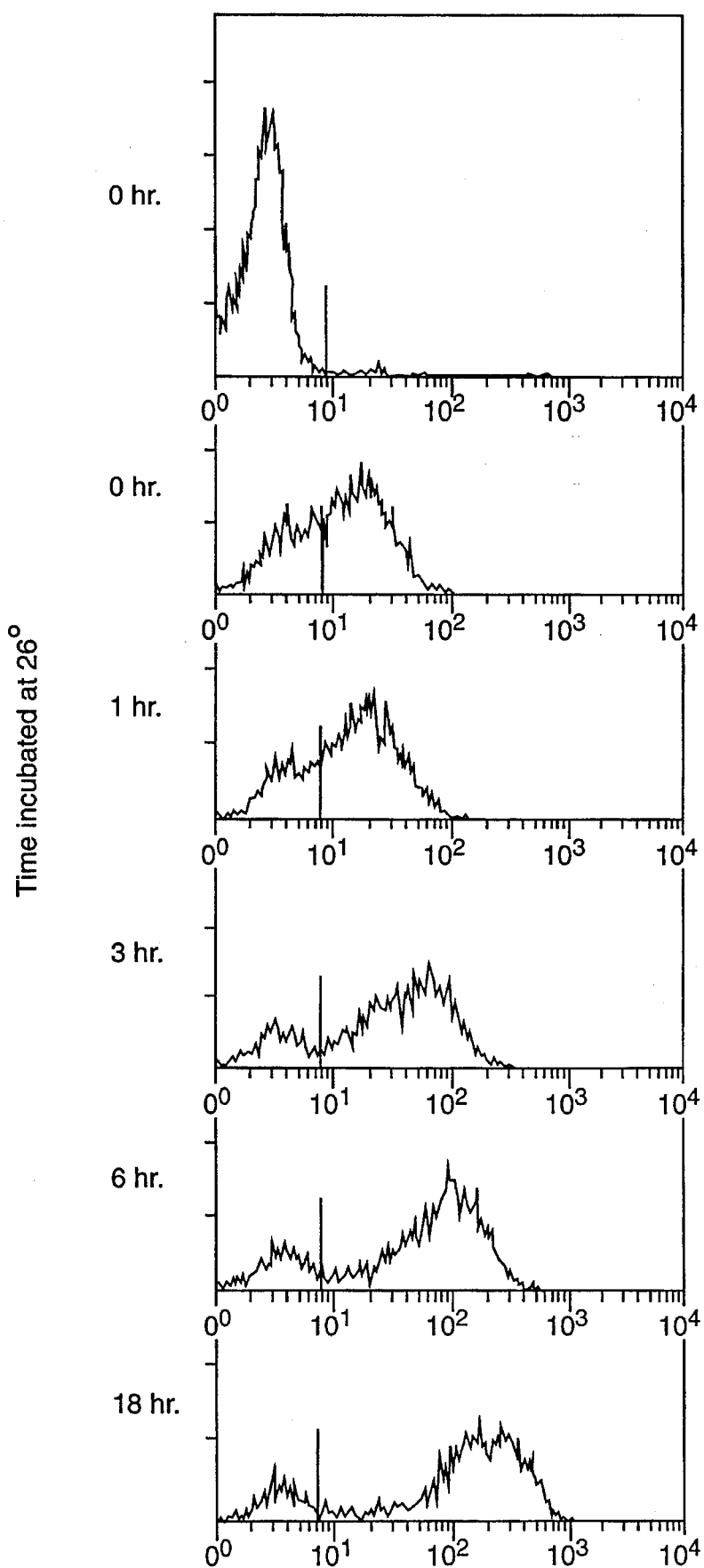
FIGS. 1B–1F show the result of the flow cytometry analysis of ClR cells transfected with mutant HLA-A201 genes that were incubated at 26° C. for 0, 1, 3, 6 and 18 hours, respectively stained with HLA-A2 and HLA-A28-specific antibody and fluoresceinated goat-anti-mouse Ig. The top panel.
FIG. 1A is a negative control. Relative cell number is shown as a function of fluorescence intensity.

As used herein, the term "Major Histocompatibility Complex (MHC)" refers to a genetic region found in all mammals whose products, including but not limited to class I and class II molecules, function in the presentation of peptides to effector T lymphocytes. In the human, this complex is denoted as HLA. In the mouse, this complex is denoted as H-2. Effector T cells are restricted by, and react to, autologous (self) MHC products. MHC molecules expressed on cells contain an antigen-binding site (ABS) in which peptides may be bound and presented to form "MHC-peptide complexes" and constitute "MHC-bound peptides." For example, "class I molecules" are presented to T cells and T cell recognition of such peptides is considered to occur in the context of such MHC molecules/complexes.

"242K cells," "242K mutants," and "242K transfectants" are cells transfected with a mutated class I MHC heavy chain gene coding for lysine instead of glutamine at position 242 in the $\alpha_3$ domain of the heavy chain of class I molecules. This mutation renders the class I molecule synthesized by these cells "temperature sensitive," meaning that the class I molecule is capable of being expressed at the cell surface at temperatures in the range of between about 20°–30° C., but not at normal body temperature (37° C.).

The term "antigen" is defined as a molecule which induces clonal lymphocytic proliferation and the generation of antigen-specific immunoglobulin from B lymphocytes and/or the generation of antigen-specific effector T lymphocytes.

"Epitope" or "antigenic determinant" refer to the relevant portion of an antigen that is recognized by effector cell receptors (i.e., immunoglobulin or T cell receptors). "T cell epitope" refers to a peptide that is presented on the cell surface of a target cell that is bound to an MHC gene product/molecule and which is recognized by a T cell.

"Immunogenic" refers to the capacity of a substance or molecule (generally a protein or protein fragments (peptides)) to serve as an antigen.

The terms "peptide-loading" and "peptide pulsing" refer to the process by which exogenous peptides are incubated in the presence of target cells in order to establish an equilibrium that results in the occupation of MHC molecule antigen binding sites by these same exogenous peptides.

A "target" is a cell that elicits an effector cell response. Positive T effector cells only respond to target cells that express the relevant MHC-encoded gene products presenting relevant T cell epitopes.

The term "effector" or "effector cell" refers to a lymphocyte that mediates an antigen-specific response. The effector cell responses may include, but are not limited to, proliferation, cytotoxicity, and/or secretion of factors (immunoglobulin or cytokines by B cells, cytokines by T lymphocytes).

The terms "elute," "remove," "release," "extract," and "strip" are used interchangeably to mean the physical removal or dissociation of T cell epitopes/ peptides from MHC molecules expressed on the surface of viable cells.

"Viable" or "viability" refers to the maintenance of physical integrity of a cell and the ability of the cell to metabolically regenerate membrane components including MHC molecules after release of MHC-bound peptides resulting from selectively shifting temperature.

II. Methods

According to the present invention methods are provided for synthesizing class I molecules with mutant heavy chains by genetically engineering class I HLA proteins. Such mutant heavy chains are unstable at body temperature, about 37° C., but are stable at lower temperatures in the range of between about 20°–30° C. It was found that mutant heavy chains bind with $\beta_2$m and are transported to the cell surface at about 26° C., but not at about 37° C. Thus at 37° C. the present invention provides method of amplifying an intracellular pool of heavy chains before they are assembled with $\beta_2$m. Then upon temperature change to 26° C., the assembled class I molecules are transported to and expressed on the cell surface.

The present invention also provides an improved and novel method of obtaining MHC-bound peptides from the cell surface of viable cells which is rapid, non-toxic to the cells, and which uses far fewer cells than methods that employ cell cytolysis, affinity purification, or low pH treatment. Additionally, only cell surface-associated peptides are removed by this method whereas other methods extract total cellular MHC-associated peptides.

As reported by Salter R. D. et al, *Nature* 345:41 (1990), the disclosure of which is incorporated herein by reference, a panel of 45 site-directed mutants, each bearing single amino acid substitutions in the $\alpha_3$ domain of the class I molecule HLA-A201/HLA-A2.1, were generated and transfected into the HLA-A2 B-negative B lymphoblastoid cell line ClR as described in Salter, R. D., et al., *J. Exp. Med.* 166:283 (1987), the disclosure of which is incorporated herein by reference, and screened for surface expression by antibody binding. ClR cells were deposited with the American Type Culture Collection, Rockville, MD on Apr. 27, 1995 under ATCC accession no. CRl 11878. For site-directed mutagenesis, a 1.5 Kb KPNl/NcoI fragment of the HLA-A2.1 gene spanning exons 3–5 was subcloned into M13mp18. Oligonucleotides were generated to convert codons that would be translated to specific amino acid residues as described by Salter, R. D., et al., *Nature* 345:41 (1990).

The mutagenesis method of Kunkel (Kunkel, T. A. *P.N.A.S. USA* 82:488 (1985) and Kunkel, T. A., et al., *Methods Enzymol.* 154:367 (1987), the disclosures of which are incorporated herein by reference) was performed with a kit by Bio-Rad (Richmond, CA). All of the mutations were confirmed by dideoxy sequencing of the inserted DNA and were then reinserted into the full-length 5.1 Kb Hind III fragment containing the HLA-A2.1 gene by ligation after digestion with Bgl II and All II. Mutants were subcloned into the vector pHEBO described in Sugden, B., et al., *Mol. Cell. Biol.* 5:410 (1985), the disclosure of which is incorporated herein by reference, and transfected into ClR cells using a BTX (San Diego, CA) electroporator. The resulting transfectants were grown in growth medium consisting of RPMI 1640 media containing 10% fetal calf serum (FCS) (Gibco, Grand Island, NY) or transfertin-supplemented calf serum (Hyclone, Logan, Utah) and 300 µg/ml hygromycin (Sigma, St. Louis, MO), hereinafter refered to as "growth medium." Surface class I levels on transfectants were measured by flow cytometry.

C1R cells transfected with mutant HLA-A201 genes were grown at 37° C. in growth medium and stained with the HLA-A2, A28-specific antibody CR11-351 (a gift, and available on request, from Peter Parham, Stanford University, Stanford, CA) and fluoresceinated goat-anti-mouse Ig (Sigma). The transfectant samples were then analyzed for class I levels on the cell surfaces by flow cytometry.

For all flow cytometry analyses described herein a total of $2-4 \times 10^5$ cells were incubated with 50 µl of hybridoma supernatant or purified monoclonal antibody for 45 minutes at 4° C. The cells were then washed twice in Dulbecco's phosphate-buffered saline (PBS) (Gibco) containing 1% bovine serum albumin (BSA) (Sigma) and 0.02% sodium azide, and then resuspended in fluoresceinated goat-anti-mouse Ig (Sigma) for 30 minutes at 4° C. The cells were then washed three times with PBS and resuspended in PBS containing 4% formaldehyde. The samples were analyzed on a Becton-Dickenson FACStar flow cytometer (Becton-Dickenson, Mountainview, CA). The gain setting (laser amplifier) was set by the operator each time the cytometer was run based on a negative control sample. Since this control varies from run to run, the mean fluorescence channel scale was arbitrarily set for each run, although within each run the fluorescence scale was uniform and proportional.

Shown below in Table I are the amino acid substitutions in the $\alpha_3$ domain of the class I heavy chain that affect class I HLA surface levels for C1R cells transfected with the corresponding mutant HLA-A201 genes. The values shown are percentages of the mean fluorescence of an HLA-A201 C1R control. Mutants that are marked by an asterisk (*) are at positions in close proximity to residues in $\beta_2m$ as defined by a decrease in contact surface area of at least 10% as compared with free side-chain domains.

TABLE 1

| Mutant | Position | Mutation | Expression Relative To HLA-2.1 (%) |
| --- | --- | --- | --- |
| 210S | 210 | pro > ser | 25 |
| 215A | 215 | leu > ala | 34 |
| 217A | 217 | trp > ala | 17 |
| 228E | 228 | thr > glu | 2 |
| 230P | 230 | leu > pro | 31 |
| 242K* | 242 | gln > lys | 5 |
| 244A* | 244 | trp > ala | 30 |
| 246V | 246 | val > ala | 9 |

As defined above, cells transfected with HLA-201 genes that express a mutation in class I heavy chains at position 242 of the $\alpha_3$ domain from gln (Q) to lys (K) are referred to as "242K cells" or "242K mutants." In addition to C1R cells, other human B lymphoblastoid cell lines and other class I negative cell lines may be transfected with mutant HLA-A201 genes in accordance with the present invention.

In the following example, cells transfected with various mutant class I genes were incubated at reduced temperatures.

EXAMPLE 1

C1R cells transfected with three of the mutants shown in Table 1: one at a residue contacting $\beta_2m$ (242K), one on the same strand but further from $\beta_2m$ (246V), and another on the opposite face of the $\alpha_3$ domain (228E) were grown in growth medium at 37° C. temperature, stained with MAbs BB7.2 (available from American Type Culture Collection ("ATCC") Rockville, MD) and CR11-351 (a gift, and available on request, from Dr. Peter Parham, Stanford University), and the surface expression analyzed by flow cytometry as described above. It was found that antibodies BB7.2 and CR11-351 bound strongly to cells that were transfected with the 242K and 246V mutants after the cells were preincubated at temperatures ranging from 21° C. to 30° C. It is believed that both of these mutations might distort strand 5 of the $\alpha_3$ domain which contact $\beta_2m$.

The 242K mutants were then grown at 26° C. for 0, 1, 3, 6, and 18 hours before the cells were stained with CR11-351 or CVC7 (a gift, and available on request, from Peter Parham, Stanford University) monoclonal antibodies and fluoresceinated goat-anti-mouse Ig. The BB7.2 MAb is specific for HLA-A2 and HLA-A69 and goat-anti-mouse Ig. CR11-351 is specific for HLA-A2 and HLA-A28 molecules and CVC7 is specific for clathrin light chain molecules and was used as a negative control. After each incubation time, the samples were then analyzed by flow cytometry as described above.

The results shown in FIGS. 1A–1F reveal that when HLA-A2.1 C1R cells are grown at 26° C., there is an increase of binding of CR11-351 with time to a maximum of 8 to 10-fold greater binding than initial levels, thereby indicating that the downshift in temperature induced transport of 242K mutant to the cell surface. In FIGS. 1A–1F relative cell number is shown on the y-axis and fluorescence intensity is shown on the x-axis. The top panel FIG. 1A is a control in which the transfectants were stained with CVC7. For the bottom 5 panels, FIGS. 1B–1F, the cells were stained with CR11-351.

The foregoing should not be interpreted to limit the present invention to HLA-A201 molecules. Class I HLA molecules in addition to HLA-A201 can be synthesized to be temperature-sensitive by substitution at position 242 of the respective heavy chains as shown below in Table 2 or at other positions of the heavy chain that render the expressed protein temperature-sensitive as described herein.

TABLE 2

| Mutant | HLA Molecule | Mutation | Mean Fluorescence Units | |
| --- | --- | --- | --- | --- |
| | | | 37° C. | 26° C. |
| A2-242K | HLA-A201 | gln > lys | 34 | 276 |
| A3-242K | HLA-A301 | gln > lys | 102 | 214 |
| A68-242K | HLA-6801 | gln > lys | 181 | 303 |
| A69-242K | HLA-6901 | gln > lys | 8 | 342 |

All four mutants tested showed increases in surface expression after incubation at 26° C. In contrast, expression of the corresponding unmutated genes in transfectants was decreased slightly by incubation at 26° C. (data not shown). Mutant class I molecules induced by shifting the temperature to 26° C. can be destabilized by shifting the cells back to 37° C., as will be shown in detail for the HLA-A201 mutant below. This suggests that it will be possible to identify peptide epitopes bound to different HLA class I molecules using as a general strategy the ability of 242K mutants to release peptides in quantities sufficient for biochemical characterization.

In the following example the binding of antibody specific for mutant class I heavy chains that were incubated at 26° C. was determined.

EXAMPLE 2

242K ClR cells were grown for 12 hours in RPMI 1640 that contained 10% FCS at 26° C. The cells were then washed twice in PBS at 4° C. The cells were then resuspended in PBS that was prewarmed to either 26° C. or 37° C. and incubated from 0–30 minutes at both temperatures separately. Aliquots of the incubated cells were stored on ice until all incubations were complete and the cells were then stained for flow cytometric analysis with BB7.2 monoclonal antibody. The results shown in Table 3 below are expressed in mean fluorescence units ("MFU") which were converted from mean fluorescence channels. OKT3 MAb, which is specific for a T cell receptor subunit (Becton-Dickenson), was used as a negative control for binding and had an MFU value of 5.

TABLE 3

| Incubation Time (Min) | Mean Fluorescence Units | |
| --- | --- | --- |
| | 37° C. | 26° C. |
| 0 | 349 | 363 |
| 5 | 226 | 372 |
| 10 | 133 | 359 |
| 15 | 88 | 340 |
| 20 | 46 | 276 |
| 25 | 46 | 334 |
| 30 | 38 | 319 |

It is readily seen that in the absence of exogenous $\beta_2$m, cells grown in PBS at 26° C. then exposed to a shift in temperature back to 37° C. rapidly lose reactivity with the HLA-A2-specific antibody BB7.2. Within 10 minutes after the shift to 37° C. a greater than loss of reactivity with BB7.2 was shown. This indicates that $\beta_2$m has dissociated from the 242K heavy chain and can no longer bind antibody BB7.2.

Figure 2A:
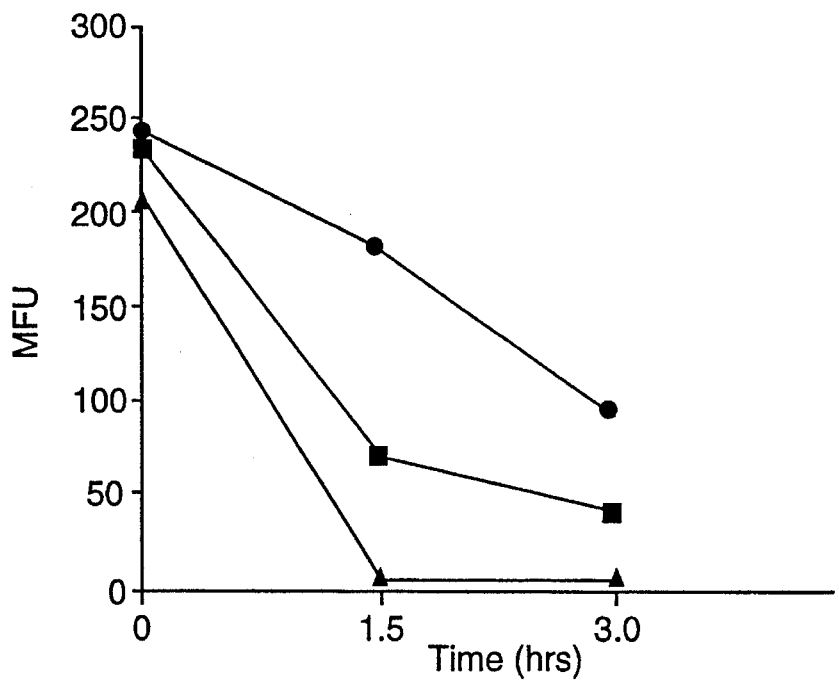
FIGS. 2A and 2B are graphs showing results of studies with ClR cells transfected with mutant HLA-A201 genes that were incubated for 18 hours with no $\beta_2$m (triangle), 0.3 µg/ml $\beta_2$m (square), or 1.0 µg/ml $\beta_2$m (circle) at either 37° C. or 26° C., respectively. The cells were stained with HLA-A2-specific antibody and fluoresceinated goat-anti-mouse Ig and analyzed by flow cytometry. Mean fluorescence units ("MFU") are shown as a function of time.
Figure 2B:
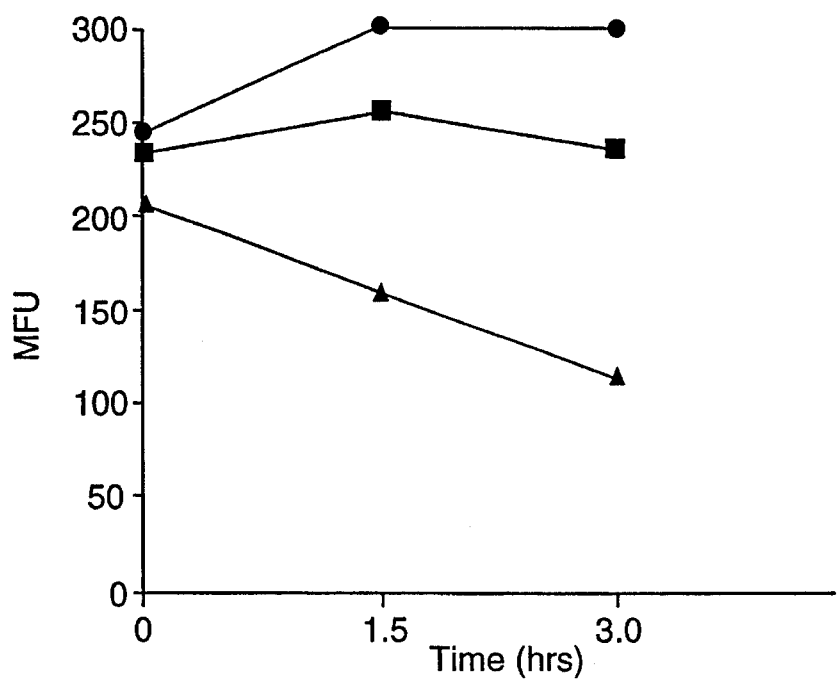

The effect of exogenous human $\beta_2$m on the dissociation of 242K mutants that were induced at 26° C. was assessed as follows. 242K ClR cells were grown for 16 hours in RPMI 1640 medium that contained 10% FCS. The cells were then washed twice in PBS, and then were incubated in PBS that contained no $\beta_2$m (triangle), 0.3 μg/ml $\beta_2$m (square), or 1.0 μg/ml $\beta_2$m (circle), at either 37° C. or 26° C. for 0, 1.5, and 3.0 hours. $\beta_2$m (Sigma) was resuspended at mg/ml in PBS. The cells were then stained as in Example 1 except that only BB7.2 was used as the antibody. The results are shown in FIG. 2A for the incubations conducted at 37° C. and in FIG. 2B for the incubations conducted at 26° C. Mean fluorescence units (MFU) are shown on the y axes.

For the incubations shifted from 26° C. to 37° C. (FIG. 2A) the expression of class I molecules on the cell surfaces was stabilized by greater than 50-fold by addition of 1 μg/ml of human $\beta_2$m to the cells. Mutant class I molecules induced by incubation at 26° C. and incubated in PBS at 26° C. (FIG. 2B), showed a slight decay in the class I molecules over 3 hours, but the decay was prevented by the addition of exogenous $\beta_2$m, with the stabilization/reverse most evident in cells treated with the higher concentration of $\beta_2$m. Mutant cells incubated in medium containing FCS also slowed the decay of class I complexes to a lesser extent, thereby indicating that bovine $\beta_2$m might similarly stabilize 242K heavy chains. (Data not shown.)

Similar studies with another HLA-A2-specific antibody, CR11-351, showed similar results. Comparable results were also obtained after 242K transfectants were initially grown for 16 hours at 26° C. in medium that contained 10% human serum. Similarly treated HLA-A201 transfectants show a less than 5% decrease in BB7.2 binding after incubation at 37° C. (Data not shown) Such results indicate that after the temperature was shifted to 37° C., the expressed class I dimers containing the position 242 mutation in the heavy chain were rapidly destabilized and dissociated into individual subunits. By contrast, expression of wild-type HLA-A201 on transfectant control cells did not change significantly over several hours during incubation at either temperature.

In the following example it was determined whether peptides bound to class I complexes (T cell epitopes) on the surfaces of target cells were released into the supernatant along with $\beta_2$m once the class I molecules expressed on the surface of 242K cells decay at 37° C.

EXAMPLE 3

Figure 3:
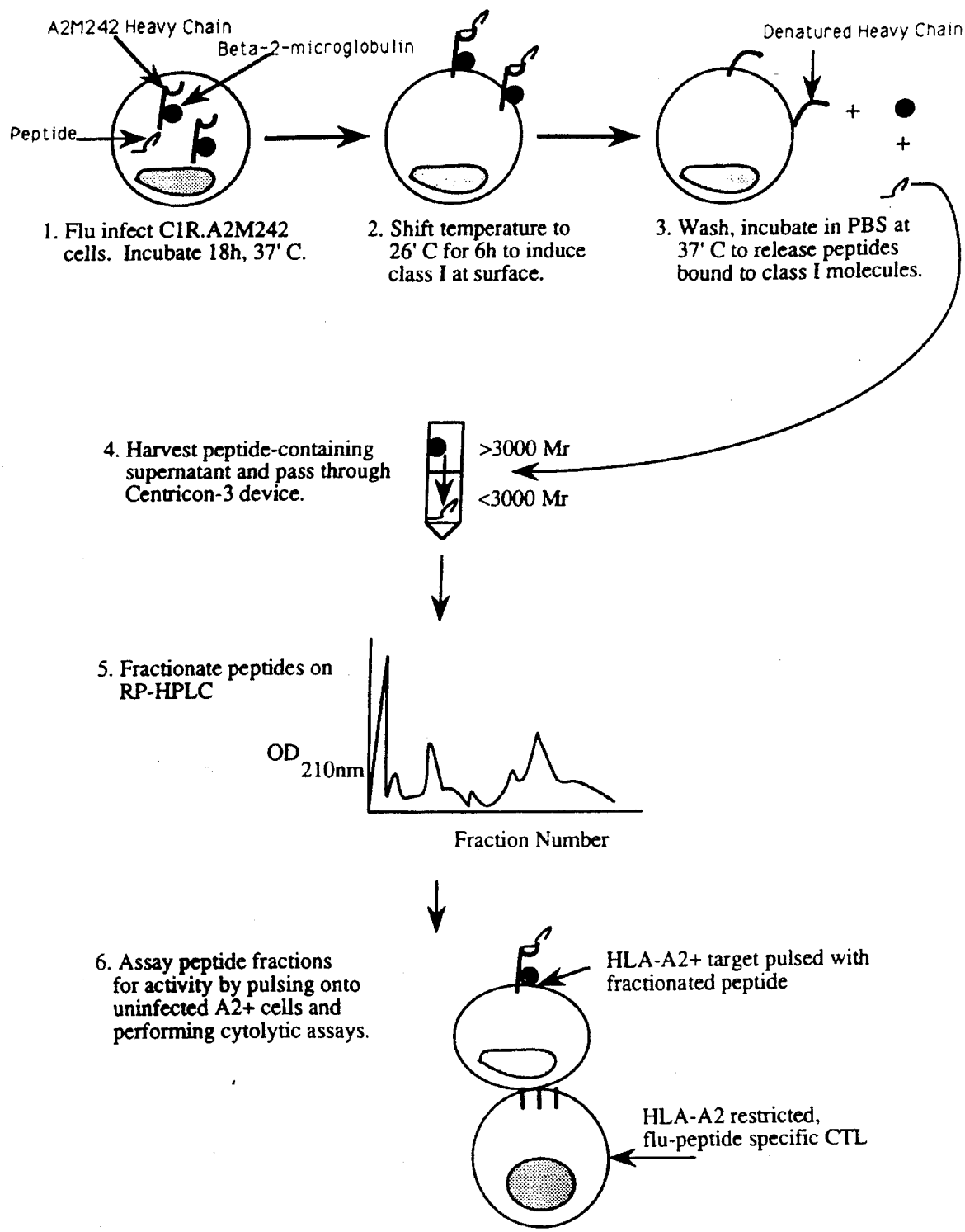
FIG. 3 is schematic representation of class I-associated peptide release from ClR.A2M242 cells.

As schematically shown in FIG. 3, ClR.A2M242 (242K transfected) cells were infected with influenza A/UDORN for 18 hours at 37° C. as described below in order to cause virus-derived, class I-presented peptides to be expressed at target cell surfaces. The infected cells were then grown at 26° C. for 6 hours to induce expression of class I complexes and class I-presented peptides on the cell surface.

The ClR.A2M242 cells were infected with the flu virus by centrifuging $4 \times 10^8$ cells at low speed (~1000 × g). The resulting cell pellet was resuspended in RPMI 1640 medium without serum, then centrifuged again. The centrifugation and resuspension steps were repeated twice. The cells were then resuspended in 10 ml of RPMI 1640 without serum that contained influenza virus stock (1 ml of stock containing $4 \times 10^8$ plaque forming units (pfu)) and incubated for 1 hour at 37° C. After incubation, 400 ml of RPMI 1640 containing 10% FCS was added and the cells were grown for 18 hours. After further incubation at 26° C. for 6 hours the cells were washed three times by resuspension in PBS, followed by low speed centrifugation, resuspension in PBS and incubation for 20 minutes at 37° C. to cause decay of the class I molecules expressed on the surface of 242K cells and concomitant release of peptides that were bound to class I molecules.

The peptides in the resulting cell free supernatant that were ≤3,000 Mr were isolated by fractionation on Centricon-3 ultrafiltration devices (Americon, Cambridge, MA) according to the manufacturer's Frotocol. The resulting bulk peptides were then either assayed directly or fractionated by liquid chromatography (LC), preferably reverse phase high performance liquid chromatography (RP-HPLC).

Briefly, the bulk peptides were fractionated on a $C_{18}$ reverse-pha se (RP) column (Alltech, Deerfield, IL) using an Eldex, (San Carlos, CA) programmable pump in a 99.92% water/0.08 % trifluoroacetic acid (TFA) to 39.935 water/0.07% TFA/ 60% acetonitrile gradient. The flow rate was maintained at 1.0 ml/minute and 1 ml fractions were collected. Each incremental gradient was linear. The HPLC runs were monitored for peptides species by monitoring the absorbence of the peptides at 210 nm using a multi-diode array detector (Linear UVIS, Reno, NV).

The resulting peptide fractions were then assayed for activity by pulsing them onto K4B B cell targets (EBV-transformed B cell lines which are HLA-A2$^+$, a gift, available on request, from Dr. William Biddison, NIH, Bethesda, MD), which target cells had been labeled with $^{51}$Cr by incubating the cells with 100 μCi of Na$_2$$^{51}$CrO$_4$ (New England Nuclear, Boston, MA) and then further incuba ting the cells for 1 hour at 37° C. The cells were washed twice with HBSS at pH 7.4 to remove free label. To determine whether released peptides contained sequences derived from influenza proteins, anti-influenza CTL lines were used in lytic assays as described below.

Anti-influenza peptide CTL lines were generated by the method of Carbone, F. R., et al., *J. Exp. Med.* 167:1767 (1988), the disclosure of which is incorporated herein by reference. Briefly, 40–60×10$^6$ peripheral blood lymphocytes (PBLs) were obtained from normal, healthy HLA-A2+ donors by venipuncture. Ficoll-Hypaque separations were then performed using the lymphocyte separation medium (LSM) kit according to the manufacturer's protocol (Organon Teknika). Peripheral blood primary stimulations were performed as follows: the lymphocytes were cultured in 10 ml of AIM-V media (Gibco) for 7 days that contained 25 µg/ml of the synthetic influenza matrix nonameric peptide Flu M1 57-68 (KGILGFVFTLTV-Lys-Gly-Ile-Leu-Gly-Phe-Val-Phe-Thr-Leu-Thr-Val) (SEQ ID No: 1) which was synthesized by the Peptide Synthesis Facility, Shared Resource, Pittsburgh Cancer Institute, Pittsburgh, PA. Weekly restimulations were then performed by taking 5×10$^6$ viable responders and adding 10$^7$ irradiated (3,000 rad) HLA-A2+ allogenic PBLs in 10 ml of AIM-V media supplemented with 25 µg/ml Flu M1 (SEQ ID No.: 1) peptide plus 50 IU/ml rhIL-2 (Chiron, Emeryville, CA). Fresh AIM-V media with 50 IU/ml rhIL-2 was added to rapidly proliferating T cell cultures as was needed.

The GL1 anti-Flu CTL line was selected for use after tertiary boosting and after display of specific recognition of Flu M1 (SEQ ID No.: 1) peptide that was presented in the context of HLA-A2 expressed by melanoma or B cell targets. GL1 lysed both influenza A/UDORN infected HLA-A2+ targets or Flu M1 (SEQ ID No.:1) peptide-pulsed HLA-A2+ targets, but not control uninfected, CIR or other non-A2 targets. (Data not shown.) The GL2P2 CTL line was raised in a similar fashion and had an identical reactivity pattern. Another CTL line, GL2V5 was generated using target PBL which had been infected with influenza virus rather than having been incubated with the synthetic Flu M1 (SEQ ID No.: 1) peptide. All three CTL lines are reactive with HLA-A2+ targets that are either infected with influenza virus or pre-incubated with Flu M1 (SEQ ID No.: 1) peptide.

In order to determine whether processed peptides are released into surrounding supernatant during decay of class I molecules at 37° C., A2.1-CIR targets and K4B B cell targets were labeled with $^{51}$Cr as described above and incubated with the peptides released from 242K cells that were infected with influenza virus obtained as described above. As a control, A2.1-CIR cells were identically infected and treated to obtain a Centricon elute as described above for the 242K CIR.A2M242 cells.

Briefly, the labeled target cells were incubated with 2.5 µg of Flu M1 57-68 (SEQ ID No.: 1) peptide or 3×10$^5$ cell equivalents of the 242K or A2.1Centricon eluates for 2 hours at 26° C. Standard 4 hour cytotoxicity assays with GL1 CTL effector cells were then carried out on the labeled target cells after washing in HBSS to remove free peptides. In order to perform the cytotoxicity assays 100 µl of target cells were loaded into each assay well of 96-well U-bottomed microculture wells at 10$^4$ targets/well. Direct target sensitivity to GL1 (anti-Flu M1 peptide-specific, HLA-A2 restricted) CTL was assessed by adding GL1 effector cells at an effector-to-target ratio of 1:1. The cells were then incubated for 4 hours at 37° C. The control, spontaneous release, constituted target cells and TCM only (for assays involving peptides this constituted 100 µl of target cells plus 125 µl of TCM; if no peptides were involved, targets and TCM were used at 100 µl each). The maximum release control consisted of 10$^4$ target cells plus 100 µl of Triton X-100 (Sigma (10% in ddH20)) in directed assays or 125 µl of Triton X-100 in peptide pulsing assays. After the 4 hour incubation, the contents of the 96-well plates were centrifuged at 50 × g for 5 minutes to pellet the cells, and 100 µl of supernatant was harvested for counting in an LKB gamma counter (Pharmacia, Piscataway, NJ). The results are shown below in Table 4.

TABLE 4

| | % Lysis | |
|---|---|---|
| Sample Added | A2.1-C1R | K4B |
| — | 5 | 9 |
| 242K extract | 37 | 51 |
| A2.1 extract | 8 | 16 |
| m1 57–68 (SEQ ID NO: 1) | 40 | 44 |

These results clearly show that the peptide released from the 242K cells was capable of sensitizing uninfected A2.1-bearing CIR cells such that flu-specific HLA A2.1-restricted cytotoxic T lymphocytes (CTL) caused lysis of the targets as efficiently as synthetic ml peptide. By contrast, A2.1 cells that were infected and treated identically did not release peptides that were capable of sensitizing uninfected A2.1 targets. This demonstrates that peptide release is a unique property of 242K cells that is not found in unmutated A2.1 molecules.

Figure 4:
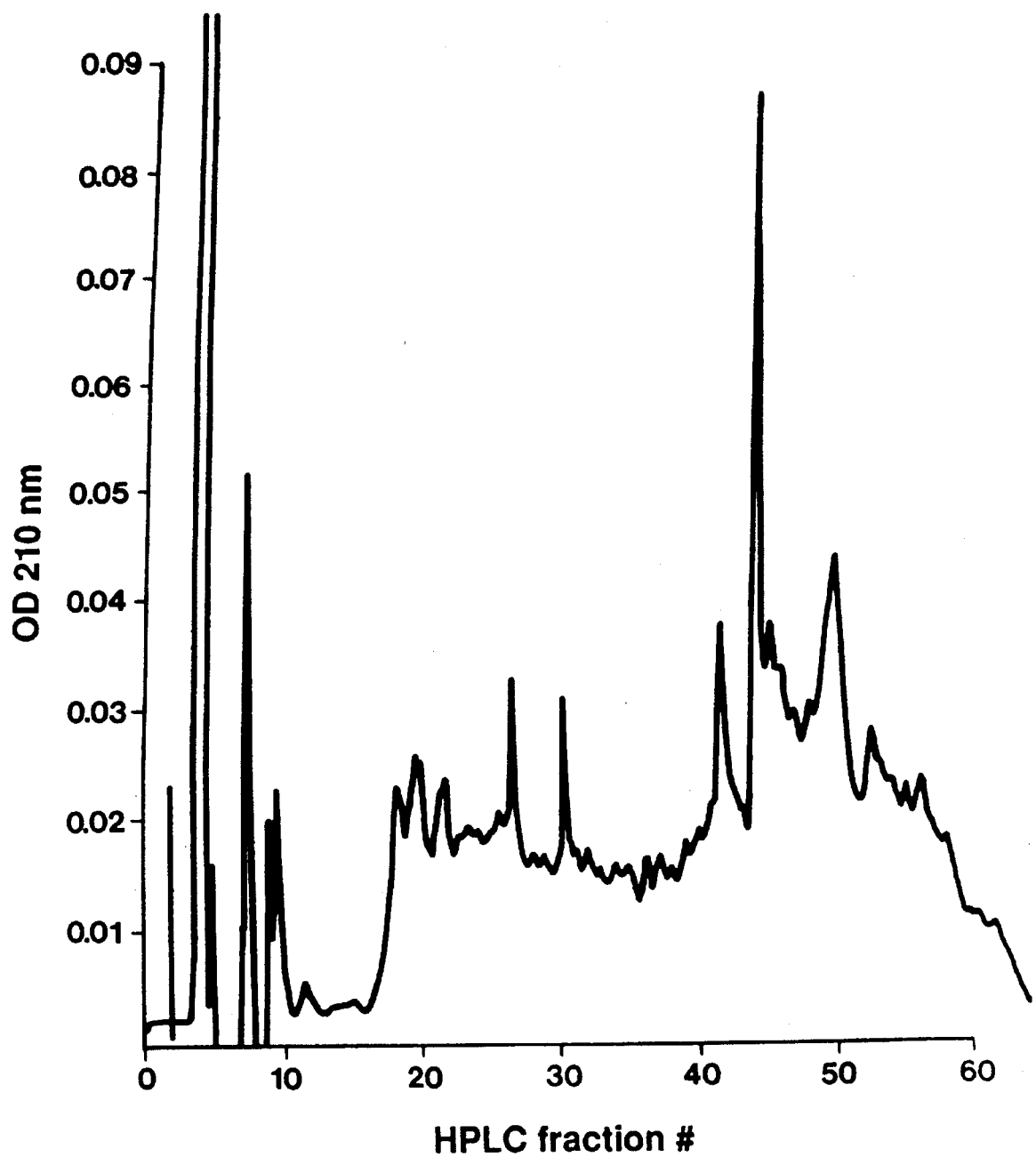
FIG. 4 shows an RP-HPLC chromatogram of 37°-released peptides from 242K cells infected with influenza virus monitored at 210 nm.

To investigate the exact nature of the influenza-derived peptides released from 242K cells in these experiments, Centricon-fractionated material was next separated by HPLC as described previously in order to purify the bioactive peptides to allow for their chemical characterization. 242K CIR cells (4×10$^8$) were infected with influenza virus as described above, induced to express their class I molecules by shifting the temperature to 26° C., and then destabilized by incubating the cells at 37°, as described above. After isolating the ≦3000 dalton material by passage over a Centricon-3 ultrafiltration device, samples were loaded onto a C$_{18}$ reverse-phase (RP) column (Alltech, Deerfield, IL). The results of the separation are shown in FIG. 4. Discrete peaks were evident by monitoring the resulting fractions at O.D. 210.

Figure 5A:
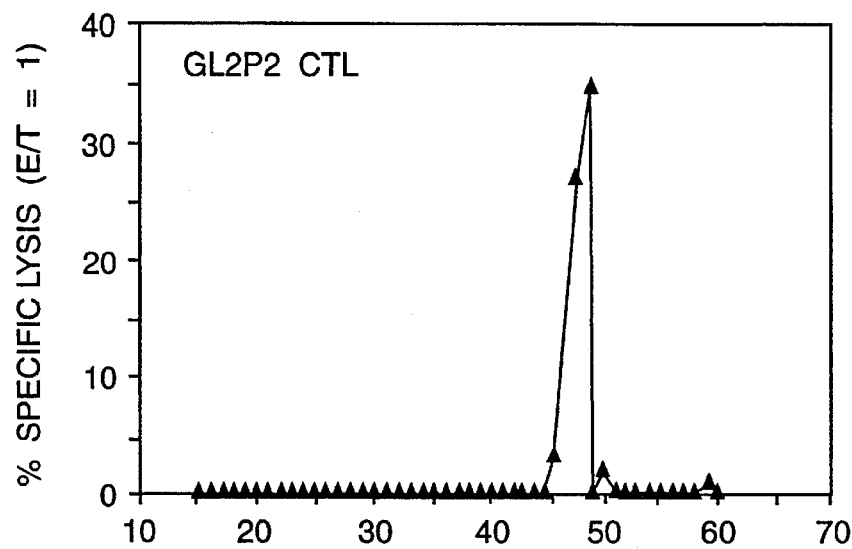
FIGS. 5A and 5B are graphs showing T cell reactivity with individual fractions that were separated by HPLC. Fractions were incubated with $^{51}$Cr-labeled K4B cells before standard 4 hour cytolysis assay with GL2P2 CTL (FIG. 5A) and GL2V5 CTL lines (FIG. 5B). Percent specific lysis is shown as a function of fraction number.
Figure 5B:
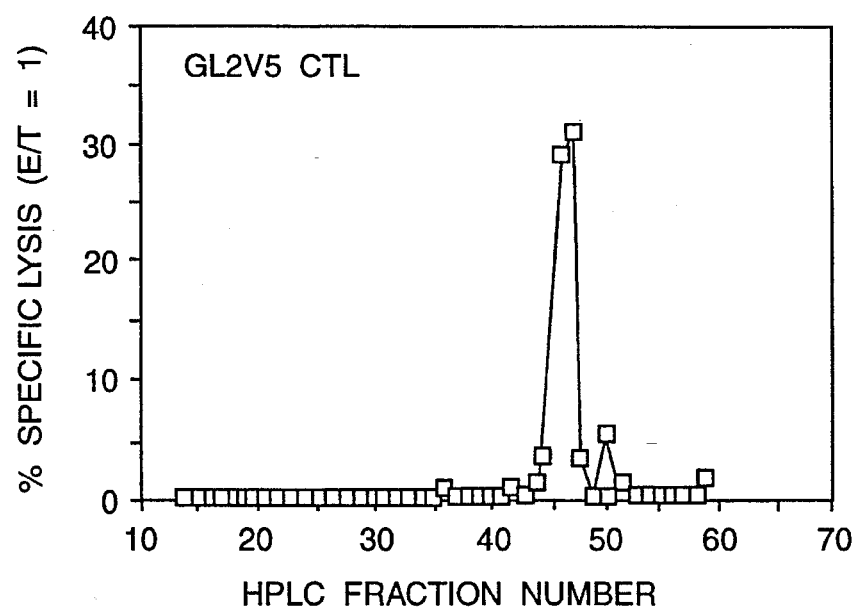

To determine which of these peaks contained the CTL-sensitizing activity, individual fractions were dried by evaporation, resuspended in PBS, then incubated with $^{51}$Cr-labeled K4B targets as described above. Targets were then incubated with either GL2P2 CTL or GL2V5 CTL in a standard 4 hour chromium release assay. The results are shown in FIG. 5. Two peak fractions (numbers 47 and 48) were identified based on absorbance at 210 nm. The synthetic peptide corresponding to Flu M1 58–66, positions 2–10 of SEQ ID No.:1) migrated at exactly this same position in the gradient, providing evidence that 242K mutants released a naturally processed peptide of the Flu M1 protein with identity to this sequence.

Although the invention has been described in detail for the purpose of illustration, it is to be understood that such detail is solely for that purpose and that variations can be made therein by those skilled in the art without departing from the spirit and scope of the invention except as it may be limited by the claims.

I claim:

1. A method of obtaining peptides that are bound to class I major histocompatibility complex "MHC" molecules expressed on the cell surfaces of viable cells that have been transfected with genes for temperature-sensitive mutant class I molecules, said genes containing a mutation than codes for lysine instead of glutamine at position 242 of the $\alpha_3$ domain of the class I heavy chain, comprising the steps of:

incubating said cells at about 37° C. in culture media;

incubating said cells at about 20°–30° C. to allow expression of MHC-peptide complexes on the surfaces of said cells;

incubating said cells at about 37° C. to cause dissociation of said peptides from the MHC-peptide complexes; and recovering said peptides from the culture media.

2. The method of claim 1, wherein said genes code for HLA-A201 heavy chains.

3. The method of claim 2, wherein said cells that are transfected are ClR B cells.

4. A method of obtaining peptides that are bound to class I MHC molecules expressed on the cell surfaces of viable cells that have at least one MHC-peptide complex presented on the surfaces of said cells, said method comprising:

transfecting cells with mutant genes that code for class I MHC heavy chain molecules such that the expressed class I molecules contain a mutation causing the class I MHC molecules to be unstable at about 37° C. but which are stable at lower temperatures, said mutant genes containing a mutation that codes for lysine instead of glutamine at position 242 in the $\alpha_3$ domain of the heavy chain;

inducing said transfected cells to express their class I HLA molecules by shifting the temperature to the range of between about 20°–30° C.;

destabilizing the expressed class I HLA molecules by shifting the temperature to about 37° C.;

and recovering peptides that had been bound to class I molecules.

5. The method of claim 4, wherein said genes code for HLA-A201 heavy chains.

6. The method of claim 5, wherein said cells that are transfected are ClR B cells.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 12 amino acids
( B ) TYPE: amino acid
( D ) TOPOLOGY: linear ( i i ) MOLECULE TYPE: peptide ( i i i ) HYPOTHETICAL: no ( i x ) FEATURE:
( A ) NAME/KEY: Flu M1 57- 68
( D ) OTHER INFORMATION: synthetic peptide ( x i ) SEQUENCE DESCRIPTION: SEQ ID NO: 1:

Lys Gly Ile Leu Gly Phe Val Phe Thr Leu Thr Val
1               5                       10